| United States Patent [19] | [11] | 4,157,984 |
| Zilliken | [45] | Jun. 12, 1979 |

[54] ANTIOXIDANTS, ANTIOXIDANT COMPOSITIONS AND METHODS OF PREPARING AND USING SAME

[75] Inventor: Fritz W. Zilliken, Remagen, Fed. Rep. of Germany

[73] Assignee: Z-L Limited, Janesville, Wis.

[21] Appl. No.: 804,594

[22] Filed: Jun. 8, 1977

[51] Int. Cl.$^2$ .............................................. C09K 15/06
[52] U.S. Cl. ................................................... 252/407
[58] Field of Search .............. 260/397.2, 398.5, 345.5, 260/397.2, 45.8 A; 252/407

[56] References Cited

U.S. PATENT DOCUMENTS

| 3,901,928 | 8/1975 | Hesse et al. | 260/397.2 |
| 3,919,268 | 11/1975 | Bose | 260/397.2 |
| 3,959,320 | 5/1976 | Salmond | 260/397.2 |
| 4,011,220 | 1/1977 | Nysted | 260/397.2 |

FOREIGN PATENT DOCUMENTS

| 1493967 | 2/1969 | Fed. Rep. of Germany | 260/345.5 |
| 50-14676 | 2/1975 | Japan | 260/345.5 |
| 50-14677 | 2/1975 | Japan | 260/345.5 |
| 50-77373 | 6/1975 | Japan. | |

*Primary Examiner*—Benjamin R. Padgett
*Assistant Examiner*—J. L. Barr
*Attorney, Agent, or Firm*—Cooper, Dunham, Clark, Griffin & Moran

[57] ABSTRACT

Antioxidants and antioxidant compositions useful as stabilizers for food compositions, including edible fats and oils, and other compositions have been prepared and recovered from a natural source, tempeh, a fermented soybean product. An ergostadientriol which possesses antioxidative properties and which in combination with mixtures of isoflavones provides compositions having exceptional antioxidative properties has been produced. This new sterol, either alone or in combination with mixtures of isoflavones or other compounds, would appear to be useful in the prevention and/or treatment of various diseases including atherosclerosis. The ergostadientriol is recovered from other constituents of a methanol extract of tempeh by a separation process based upon its molecular size and adsorptive properties. Two novel isoflavones have also been produced and recovered from tempeh. A mixture of these isoflavones possesses antioxidative properties which are enhanced by the presence of the ergostadientriol and known isoflavones. Separate recovery or production of these isoflavones is accomplished by the same method used to recover the aforementioned novel sterol. Antioxidant compositions comprising the ergostadientriol, the two new isoflavones and known isoflavones can be prepared. Also, such antioxidant compositions can be recovered from tempeh either by a method involving methanol extraction similar to that used for recovery of the sterol and the isoflavones or by a method involving petroleum ether extraction.

9 Claims, No Drawings

ANTIOXIDANTS, ANTIOXIDANT COMPOSITIONS AND METHODS OF PREPARING AND USING SAME

BACKGROUND OF THE INVENTION

Many food products containing and including edible fats and oils, i.e., fats and oils of animal and vegetable origin or modified fats and oils of animal and vegetable origin, become rancid or have an undesirable taste and/or color imparted thereto during storage, especially upon exposure to or on contact with oxygen. A number of chemical compounds have been employed for avoiding or reducing these effects so that food products containing fats or oils may be kept for longer periods of time, but such agents have not been entirely satisfactory or effective in many cases. Furthermore, such chemical compounds are usually synthetic chemical products not derived from or identical with material of natural food classifications and, as a consequence, there has been some question as to the advisability of using such compounds in food compositions.

Principal antioxidants of the above kinds heretofore employed included BHA (butylated hydroxyanisole), BHT (butylated hydroxytoluene) and TBHQ (tertiary butylhydroquinone), as well as some other chemicals of which one example is propyl gallate (PG). While these materials have been quite effective in animal fats, such as lard, they are much less useful in some other applications. Their volatility and tendency to decompose at high temperatures makes them not entirely suitable for deep fat fried foods. Indeed, their usefulness for the stability of vegetable oils is less than satisfactory. For example, they are not entirely effective in protecting against off-flavor development, such as the so-called reversion flavor, that occurs, with passage of time, in soybean oil. For these and other reasons, there has been a need for improvement in the field of antioxidants, especially those to be used with food materials that comprise or consist of fats or oils.

It has heretofore been found that antioxidant properties are possessed by tempeh, a fermented soybean product, obtained by fermenting soybeans with a fungus, either *Rhizopus oligosporus* or *Rhizopus oryzae,* and food products containing tempeh, such as fish or fatty meat food products, exhibit improved stability, see U.S. Pat. No. 3,681,085 (1972). It has further been heretofore found that by extracting tempeh with a mixture of hexane and ethanol, a component of tempeh, namely oil of tempeh, can be recovered, see U.S. Pat. Nos. 3,762,933 (1973) and 3,855,256 (1974). Oil of tempeh demonstrates improved antioxidant properties over those of unextracted tempeh. Although the aroma of tempeh and oil of tempeh is an essentially mild and pleasant one, the use of these materials is limited to situations where their basic flavors are desired or at least tolerable.

Although the chemical additives described above are essentially tasteless and odorless, their non-natural or synthetic origin creates problems. There is a need in the food industry for an antioxidant derived from natural foodstuffs and which has superior properties and can serve a wide range of uses.

SUMMARY OF THE INVENTION

The subject invention relates to the production of a novel ergostadientriol and two new isoflavones, particularly the production and recovery of these compounds from a natural foodstuff, namely, the fermented soybean product tempeh. These compounds possess antioxidative properties either alone or in combination. The present invention further relates to the production and recovery from tempeh of unusually effective and essentially tasteless and odorless antioxidant compositions containing these novel compounds, which are superior to known conventional chemical antioxidants. The compositions produced in accordance with this invention are essentially free of vitamin E.

The subject invention also relates in one embodiment to the utilization of these compositions in the stabilization of a wide variety of food products, including edible fats and oils, such as vegetable oil, corn oil, soybean oil and lard, and other products, including cosmetics. In another embodiment, this invention relates to the utilization of the new ergostadientriol prepared and recovered in the prevention and treatment of various diseases, including atherosclerosis.

It is therefore an object of this invention to prepare a novel ergostadientriol which possesses antoxidative properties and which in combination with mixtures of insoflavones yields compositions having exceptional antioxidative properties.

It is a related object to provide a method of recovering this new ergostadientriol.

It is a further object of this invention to produce two new isoflavones which possess antioxidative properties and which in compositions including the ergostadientriol provide exceptional antioxidative properties.

It is a related object of this invention to provide a method of recovering these new isoflavones.

It is another object of this invention to define antioxidant compositions comprising the ergostadientriol and mixtures of isolfavones which include the two new isoflavones.

It is yet another related object of this invention to provide methods of preparing such compositions from the constituent compounds and of recovering them from tempeh.

It is still a further object of this invention to provide food compositions having improved stability and containing antioxidant compositions which include one or more of the new compounds disclosed herein.

It is a related object of this invention to provide a method of stabilizing food products through the addition thereto of antioxidant compositions which include one or more of the new compounds disclosed herein.

It is still another object of this invention to provide edible fat and oil compositions having improved stability and containing antioxidant compositions which include one or more of the new compounds disclosed herein.

It is a related object of this invention to provide a method of stabilizing edible fat and oil compositions through the addition thereto of antioxidant compositions which include one or more of the new compounds disclosed herein.

It is another object of this invention to provide a method for utilizing the new ergostadientriol in the prevention and treatment of various diseases including atherosclerosis and the like.

How these and other objects of this invention are accomplished will become apparent in the light of the following detailed description of this invention. In at least one embodiment of the practices of this invention, at least one of the foregoing objects will be achieved.

DETAILED DESCRIPTION OF THE INVENTION

In accordance with one embodiment of this invention, a novel ergostadientriol has been prepared. This novel ergostadientriol possesses antioxidative properties. It is "Emmerie Engel" positive at the same order of magnitude as vitamin E, i.e., it reduces $Fe^{+++}$ to $Fe^{++}$ at room temperature, the latter forming a brilliant red complex in the presence of α,α-dipyridil. In combination with mixtures of isoflavones, this sterol provides antioxidant compositions with exceptional properties. This new ergostadientriol has been identified by UV, IR, and high resolution mass spectrometry to be a 3-hydroxy-ergosterol of the formula $C_{28}H_{46}O_3$ and molecular weight 430, having the following structure:

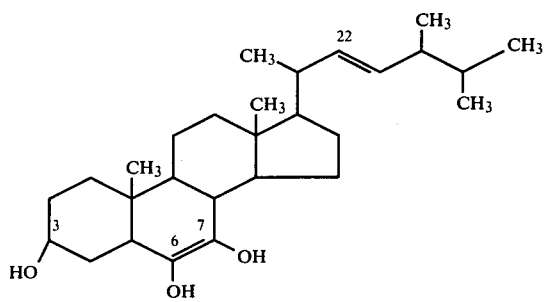

It is produced by fermentation of soybean with a fungus, either *Rhizopus oligosporus* or *Rhizopus oryzae*. The ergostadientriol has been produced and recovered from the fungus itself after growth on a suitable culture medium. Suitable fungi for producing this compound are *Rhizopus oligosporus* ATCC No. 22959 and *Rhizopus oryzae* ATCC No. 9363.

Dry, i.e., lyophilized, tempeh powder or fungus is contacted with a 60-70% aqueous methanol solution for an extended period, e.g., overnight, at a relatively low temperature, e.g., about 4° C., thereby extracting methanol-soluble components, including the ergostadientriol from the tempeh powder. The methanol extract solution, after removal of insoluble material, is evaporated to dryness in vacuo at an elevated temperature, e.g., a temperature in the range 40°-60° F., and a solid residue is produced. This solid residue is redissolved in dry methanol. The insoluble portion of this residue is separated from the soluble components by centrifugation, after which the supernatant is extracted with hexane several times, e.g., 2-3×, in order to remove any remaining traces of hexane-soluble impurities, e.g., lipids. Next, the methanol supernatant is evaporated to reduce its volume to a minimal fraction, e.g., 20 ml, and kept at a low temperature, e.g., −20° C., for a brief time, e.g., a time in the range 15-20 minutes. This results in the formation of additional precipitate which is removed. The then-remaining supernatant is subjected to molecular sieve chromatagraphy, e.g., chromatography on Sephadex LH20 using a suitable size column, e.g., 2×40 cm, and a suitable mobile phase, e.g., n-propanol/ethylacetate/$H_2O$=5:5:1. One of the fractions resulting from this chromatographic separation is fluorescent with emission in the blue range of the visible spectrum. This blue fluorescent fraction is next subjected to adsorption chromatography on a suitable matrix, e.g., silica gel, using an appropriate mobile phase, e.g., ethylacetate/propanol/$H_2O$=95:2:3. The resulting blue fluorescent fraction is then subjected to rechromatography on an adsorptive matrix, e.g., silica gel again, employing a different mobile phase, e.g., cyclohexane/dichloromethane/ethyl formate=35:30:30. The resulting blue fluorescent fraction is next subjected to thin layer chromatography on silica gel using a suitable, mobile phase, e.g., cyclohexane/dichloromethane/ethyl formate/formic acid=35:30:30:5. The ergostadientriol is recovered in essentially pure form utilizing its differential mobility on the silica gel plate as compared with other components of the blue fluorescent fraction.

In a particularly preferred embodiment, the ergostadientriol is obtained in pure form by preparative high pressure liquid gas chromatography.

In accordance with another embodiment of this invention, two new isoflavones have been produced. In admixture, these two new isoflavones provide an antioxidative composition. Mixtures containing the new ergostadientriol described above, these two new isoflavones and other known isoflavones provide exceptionally effective antioxidative compositions.

One of these two new isoflavones, identified as such by UV, IR, high resolution MASS and NMR spectrometry, has a melting point of 222° C., a molecular weight of 284, emits a bright blue fluorescence after $NH_3$ treatment when excited with UV-light, and has the structure substantially as shown by I following:

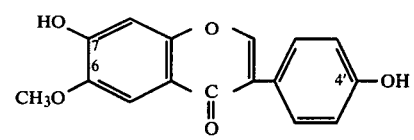

The other isoflavone, and also identified as such by UV and mass spectrometry, emits a bright green fluorescence after $NH_3$ treatment when excited with UV-light and has substantially the structure shown by II below:

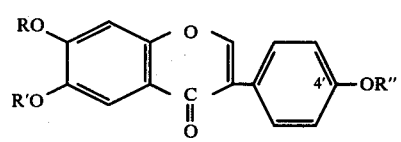

(wherein one or more R, R', R" are methyl groups and, if not methyl, then H)

In II, R and R' may be replaced by $CH_2$ to form the linkage

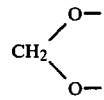

In accordance with another embodiment of this invention, these isoflavones are separately recovered from tempeh by the same process described previously to recover the ergostadientriol. The only difference is in the last step of the recovery process, namely, thin layer chromatography on silica gel. The isoflavones are separated and recovered from each other and from other components of the blue fluorescent fraction on the basis of their unique mobilities.

A mixture of these new isoflavones possesses antioxidative properties and can be used as an antioxidant composition in various applications as set forth hereinbelow. In a standard test assay involving the oxidation of lard by exposure to air at 60° C. for 72 hours, addition of a mixture of the new isoflavones at a concentration of 0.1% by weight of the mixture results in about 50% protection of the lard against oxidation. Such a mixture can be prepared by mixing the isoflavones after they have been separately recovered according to the procedure described above. Although approximately equimolar mixtures are most effective, mixtures containing as much as five times the amount of one new isoflavone in comparison with another are still effective antioxidants.

In accordance with another embodiment of this invention, antioxidant compositions comprising the ergostadientriol and mixtures of isoflavones which include the two new isoflavones have been developed. In one preferred embodiment, such an antioxidant composition comprises the ergostadientriol, the two new isoflavones and the so-called "Murata" compound (6,7,4'-trihydroxy-isoflavone). In the standard test assay involving the oxidation of lard by exposure to air at 60° C. for 72 hours, nearly 100% protection has been obtained by addition of such a composition at a concentration of 0.05% by weight. In additional preferred embodiments of this invention, antioxidant compositions comprise the ergostadientriol, the two new isoflavones, the "Murata" compound and Genistein (5,6,4'-trihydroxy-isoflavone) and/or Daidzein (7,4'-dihydroxyisoflavone). Such compositions also provide nearly 100% protection in the standard assay at concentrations of 0.05% by weight.

In accordance with still another embodiment of this invention, antioxidant compositions comprising the ergostadientriol and mixtures of isoflavones which include the new isoflavones can be prepared by mixing the ergostadientriol recovered in accordance with the procedure set forth above and the new isoflavones similarly recovered in accordance with the procedure set forth above. Additional known isoflavones (i.e., "Murata" compound, Genistein, and Daidzein) can be added as well. These known isoflavones can be recovered either in accordance with previously known methods or as side products of the procedure set forth hereinabove for recovery of the sterol and the new isoflavones. These known compounds are recovered from the silica gel plate used in said procedure based upon their known mobilities.

Additionally, an antioxidant composition comprising the ergostadientriol and a mixture of the new isoflavones and the three known isoflavones can be recovered from tempeh by the same procedure used for the recovery of the sterol and the isoflavones except that the final blue fluorescent fraction obtained is not subjected to any further treatment. This fraction is comprised of the sterol and the mixture of the five isoflavones.

Alternatively, this particular antioxidant composition can be recovered by contacting tempeh powder with petroleum ether at an elevated temperature, e.g., a temperature in the range 50°-60° C., for a short time, e.g., about one hour. The resulting petroleum ether extract containing components of tempeh soluble in petroleum ether is discarded and the residue containing insoluble components is further extracted by adding ether. Insoluble material is discarded, and the extract solution containing the antioxidant composition is evaporated to dryness. The resulting residue is washed with petroleum ether several times, e.g., three times, to remove any remaining petroleum ether-soluble material, and the remaining residue is dissolved in a mixture of $CHCl_3$:methanol containing equal portions of each. This solution containing the antioxidant composition is subjected to adsorption chromatography on silica gel using a suitable mobile phase, e.g., ether and chloroform respectively, and the antioxidant composition is recovered from the column eluent.

Additionally, this particular antioxidant composition can be recovered by contacting tempeh powder with petroleum ether (b.p. 40°-60° C.) on a continuously working Soxhlet apparatus under reflux for about one hour. The petroleum ether extract is discarded, and the tempeh powder remaining in the Soxhlet tube is treated with $N_2$ gas for a few minutes to remove the last traces of solvents. The powder is then extracted with peroxidefree ethyl ether for about three (3) hours on the same Soxhlet apparatus. This extract, which contains among other constituents the antioxidant composition, is then evaporated to dryness.

Next, the oil extract is transferred to a much smaller Soxhlet tube (e.g., 10×2 cm. in dimension) and extracted with petroleum ether continuously for about 10 minutes. The extract is discarded. Subsequently, the powder is extracted for about two (2) hours with peroxide-free ethyl ether yielding after evaporation the antioxidant composition in an essentially pure state.

In accordance with yet another embodiment of this invention, stabilized food compositions are defined comprising a food product such as fish, fatty meat, or derivatives thereof, and antioxidant compositions which include one or more of the compounds disclosed herein. An antioxidant composition comprising the two new isoflavones confers improved stability. An antioxidant composition comprising the ergostadientriol, the two new isoflavones, and the "Murata" compound confers exceptional stability, as does one which additionally includes Geinistein and/or Daidzein.

Such stabilized food compositions can be prepared by addition to food products, such as fish, fatty meat or derivatives thereof, of an effective amount of an antioxidant composition which includes one or more of the new compounds disclosed herein. Specifically, the antioxidant composition comprising the two new isoflavones confers stability when added in an amount in the range 0.01-1.0% by weight. Antioxidant composition comprising the sterol and mixtures of isoflavones as described above confer stability when added in an amount in the range 0.005-0.5% by weight, more or less.

In accordance with another embodiment of this invention, stabilized edible oil and fat compositions are defined comprising an oil or fat, such as lard, corn oil, olive oil, soybean oil or palm oil, and antioxidant compositions which include one or more of the new compounds disclosed herein. An antioxidant composition which comprises the two new isoflavones alone confers improved stability. An antioxidant composition comprising the ergostadientriol, the two new isoflavones, and the "Murata" compound confers exceptional stability, as does one which additionally includes Genistein and/or Daidzein. Such stabilized edible fat and oil compositions can be prepared by addition to an oil or fat, such as lard, corn oil, olive oil, soybean oil or palm oil, of an effective amount of an antioxidant composition which includes one or more of the new compounds disclosed herein. Specifically, the antioxidant composition comprising the two new isoflavones confers stability when added in an amount in the range 0.01–1.0% by weight. Antioxidant compositions comprising the sterol and mixtures of isoflavones as described above confer stability when added in an amount in the range 0.005–0.5% by weight, more or less. The antioxidant compositions of this invention are also useful in the preparation and stabilization of oleaginous cosmestic compositions.

In the embodiment of this invention relating to atherosclerosis, diseases which involve the formation of steroid-epoxides in vivo may be prevented and/or treated by utilization of the antioxidative properties of the ergostadientriol. This utilization is based upon the indicated ability of the sterol to prevent the formation of steroid-epoxides and thus prevent the damage done by these epoxides to mitochondrial membranes and to heart and brain vessels. The presence of such epoxides has been noted in patients suffering from a number of disorders, including atherosclerosis, and a casual relationship has been suggested. The utilization of the sterol for this purpose involves administration or introduction into a patient's internal system by an appropriate method, e.g., oral ingestion, of an effective amount of the sterol, e.g., an amount in the range 10–100 mg per 70 kg of human body weight.

Stabilized oil compositions in accordance with the practices of this invention include corn oil containing 0.01–2% by weight of the aforementioned two new isoflavones, e.g., compounds of I and II, or extracts containing the same, palm oil containing the aforementioned ergostadientriol and the aforementioned two isoflavones and extracts containing the same wherein the ergostadientriol is present in the same percentage or parts by weight as the total two isoflavones, the admixture being present in the palm oil in an amount in the range 0.005–1.0% by weight based on the palm oil. Oils protected against oxidation in the manner described herein with respect to palm oil or corn oil include soybean oil, peanut oil, safflower oil, olive oil, sunflower oil, cottonseed oil and the like. Fats including the natural fats, lard, and synthetic fats, such as are derived from hydrogenated vegetable oils, are similarly protected against oxidation in accordance with the practices of this invention by incorporating either the two isoflavones or extracts thereof in an amount in the range 0.01–1% by weight of the fat or by incorporating therein the ergostadientriol or extracts thereof in addition to the isoflavones in an amount in the range 0.001 to about 1.0% by weight based on the fat.

It is mentioned hereinabove that the ergostadientriol and the combination of the isoflavones are employed in substantially equal amounts or parts by weight in the fat or oil composition to be protected against oxidation. If desired, the ergostadientriol may be employed in parts by weight relative to the isoflavones in a ratio in the range 0.1 to 10.0 parts by weight ergostadientriol to one part by weight of the combination of the isoflavones.

As will be apparent to those skilled in the art in the light of the foregoing disclosure, many modifications, alterations and substitutions are possible in the practice of this invention without departing from the spirit or scope thereof.

I claim:

1. An antioxidant composition consisting essentially of at least two compounds having the structure:

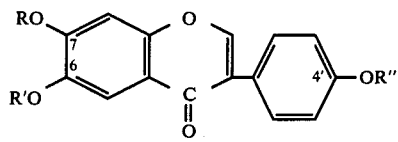

wherein each of R, R' and R" may be a methyl group or hydrogen or wherein R and R' are replaced by $CH_2$ to form the linkage

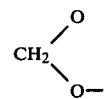

provided that one of said compounds has the structure:

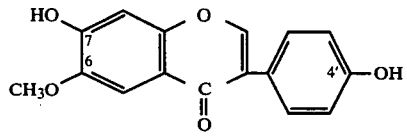

said compounds being present in amounts such that the amount of one compound relative to another is in the range 1:5 to 5:1.

2. A composition in accordance with claim 1 wherein said compounds are present in equimolar amounts.

3. A composition in accordance wiht claim 1 which includes 6,7,4'-trihydroxy-isoflavone.

4. A composition in accordance with claim 1 which includes 6,7,4'-trihydroxy-isoflavone, 5,6,4'trihydroxyisoflavone and 7,4'-dihydroxy-isoflavone.

5. A composition in accordance with claim 1 which additionally includes a compound having the structure:

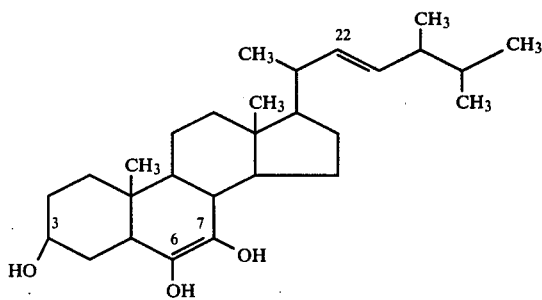

6. A composition in accordance with claim 3 which additionally includes a compound having the structure:

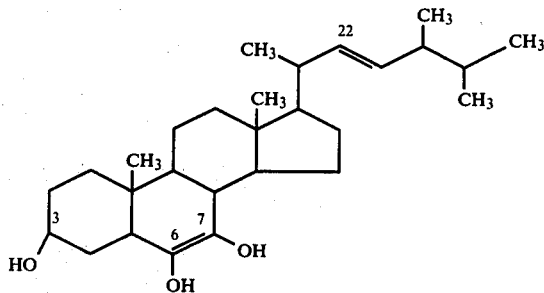

7. A composition in accordance with claim 4 which additionally includes a compound having the structure:

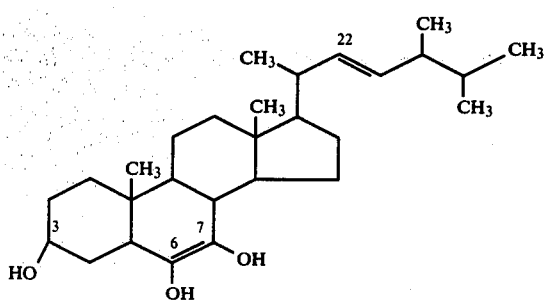

8. A method of recovering an antioxidant composition which comprises contacting tempeh with a 60–70% aqueous methanol solution at a temperature in the range 0°–10° C., evaporating the resulting methanol extract solution to dryness in vacuo to produce a residue, redissolving said residue in dry methanol, contacting the resulting methanol solution with hexane to remove contaminating material, discarding the resulting hexane extract, reducing the volume of the remaining methanol solution by evaporation at a reduced temperature for about 10–30 minutes, removing the resulting precipitate, subjecting the remaining methanol solution to chromatographic fractionation employing Sephadex LH20, the mobile phase in said chromatographic fractionation operation being n-propanol/ethylacetate/H$_2$O in the ratio 5:5:1, subjecting the resulting eluent to further chromatographic fractionation employing silica gel utilizing two mobile phases, the first phase being a mixture of ethylacetate/propanol/H$_2$O in the ratio 95:2:3 and the second phase being a mixture of cyclohexane/dichloromethane/ethylformate in the ratio 35:30:30, and recovering said antioxidant composition as eluent from said silica gel fractionation operation.

9. A method of recovering an antioxidant composition which comprises contacting tempeh with petroleum ether at a temperature in the range 40°–60° C. from 30 to 90 minutes, extracting the resulting petroleum ether insoluble residue with ether, evaporating the resulting ether extract to dryness, washing the then resulting residue with petroleum ether, redissolving said residue in a mixture of CH$_3$Cl and methanol in the ratio 1:1, subjecting the resulting solution to chromatographic fractionation employing silica gel, the mobile phase being ether, followed by chloroform, and recovering said antioxidant composition as eluent from said silica gel fractionation operation.

* * * * *

UNITED STATES PATENT AND TRADEMARK OFFICE
CERTIFICATE OF CORRECTION

PATENT NO. : 4,157,984
DATED : June 12, 1979
INVENTOR(S) : Fritz W. Zilliken

It is certified that error appears in the above-identified patent and that said Letters Patent are hereby corrected as shown below:

Cover Page, the Assignee should correctly read:
-- Z-L Limited Partnership --
Column 2, line 34, "isolfavones" should correctly read
-- isoflavones --
Column 3, 11th line from the bottom, "chromatagraphy" should correctly read -- chromatography --
Column 6, lines 17 and 18, "perox-idefree" should correctly read -- peroxide-free --
Column 8, line 15, the linkage should correctly read:

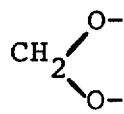

Signed and Sealed this

Eleventh Day of December 1979

[SEAL]

Attest:

SIDNEY A. DIAMOND

Attesting Officer

Commissioner of Patents and Trademarks